US010327733B2

(12) United States Patent
Lee et al.

(10) Patent No.: US 10,327,733 B2
(45) Date of Patent: Jun. 25, 2019

(54) ULTRASOUND IMAGE APPARATUS AND METHOD OF OPERATING THE SAME

(71) Applicant: SAMSUNG MEDISON CO., LTD., Hongcheon-gun (KR)

(72) Inventors: Kwang-hee Lee, Hongcheon-gun (KR); Gil-ju Jin, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 746 days.

(21) Appl. No.: 14/955,470

(22) Filed: Dec. 1, 2015

(65) Prior Publication Data

US 2016/0151041 A1    Jun. 2, 2016

(30) Foreign Application Priority Data

Dec. 1, 2014   (KR) ........................ 10-2014-0169967

(51) Int. Cl.
*A61B 8/08* (2006.01)
*A61B 8/00* (2006.01)
*A61B 8/14* (2006.01)

(52) U.S. Cl.
CPC ............ *A61B 8/0866* (2013.01); *A61B 8/085* (2013.01); *A61B 8/461* (2013.01); *A61B 8/463* (2013.01); *A61B 8/467* (2013.01); *A61B 8/5207* (2013.01); *A61B 8/5223* (2013.01); *A61B 8/14* (2013.01); *A61B 8/4405* (2013.01);
(Continued)

(58) Field of Classification Search
CPC ....... A61B 8/0866; A61B 8/085; A61B 8/461; A61B 8/467; A61B 8/463; A61B 8/5223; A61B 8/5207; A61B 8/488; A61B 8/4472; A61B 8/4427; A61B 8/4405; A61B 8/14; A61B 8/483
USPC ................................. 600/437–469
See application file for complete search history.

(56) References Cited

U.S. PATENT DOCUMENTS 5,222,485 A * 6/1993 Jerath ................. A61B 8/0866
  600/437
5,876,357 A * 3/1999 Tomer ................. A61B 5/1076
  600/587
(Continued)

FOREIGN PATENT DOCUMENTS

EP    1 905 353 A1    4/2008
JP    7116159 A       5/1995
(Continued)

OTHER PUBLICATIONS

Communication dated May 4, 2016, issued by the European Patent Office in counterpart European Application No. 15197048.0.
(Continued)

*Primary Examiner* — Sanjay Cattungal
(74) *Attorney, Agent, or Firm* — Sughrue Mion, PLLC

(57) ABSTRACT

Provided is an ultrasound imaging apparatus including: a data acquisition unit configured to acquire ultrasound data for an object including a first region and a second region used to determine a shape of the first region; a controller configured to extract the second region of the object from the ultrasound data, set at least one guide line corresponding to the first region, and measure the at least one guide line corresponding to the first region; and a display configured to display measurement information regarding the at least one guide line.

25 Claims, 16 Drawing Sheets

(52) U.S. Cl.
CPC .......... *A61B 8/4427* (2013.01); *A61B 8/4472* (2013.01); *A61B 8/483* (2013.01); *A61B 8/488* (2013.01)

(56) References Cited

U.S. PATENT DOCUMENTS

| | | | | |
|---|---|---|---|---|
| 6,101,408 | A * | 8/2000 | Craine | A61B 1/0638 |
| | | | | 128/922 |
| 6,175,751 | B1 * | 1/2001 | Maizes | A61B 5/14542 |
| | | | | 600/338 |
| 6,432,051 | B1 * | 8/2002 | Rantala | A61B 5/14542 |
| | | | | 600/309 |
| 8,237,784 | B2 | 8/2012 | Kim et al. | |
| 2004/0236193 | A1 * | 11/2004 | Sharf | A61B 5/0031 |
| | | | | 600/302 |
| 2008/0167581 | A1 * | 7/2008 | Paltieli | A61B 5/1076 |
| | | | | 600/588 |
| 2009/0093716 | A1 * | 4/2009 | Deischinger | A61B 8/0866 |
| | | | | 600/443 |
| 2011/0190580 | A1 * | 8/2011 | Bennett | A61B 1/00016 |
| | | | | 600/109 |
| 2012/0249764 | A1 * | 10/2012 | Kuon | A61B 1/05 |
| | | | | 348/67 |
| 2014/0188027 | A1 | 7/2014 | Jaber | |
| 2016/0166233 | A1 * | 6/2016 | Yoo | A61B 8/4254 |
| | | | | 600/438 |
| 2017/0020529 | A1 * | 1/2017 | Tsur | A61B 17/122 |
| 2017/0090675 | A1 * | 3/2017 | Lee | A61B 8/465 |

FOREIGN PATENT DOCUMENTS

| | | |
|---|---|---|
| KR | 10-1014562 B1 | 2/2011 |
| KR | 10-1250456 B1 | 4/2013 |
| KR | 10-1360385 B1 | 2/2014 |
| WO | 2010057665 A1 | 5/2010 |

OTHER PUBLICATIONS

Vincenzo Berghella et al: "Natural History of Cervical Funneling in Women at High Risk for Spontaneous Preterm Birth", Obstetrics & Gynecology, vol. 109, No. 4, Apr. 1, 2007, pp. 863-869, XP002756754 (7 pages total).

Iams et al: "The Length of the Cervix and the Risk of Spontaneous Premature Delivery", The New England Journal of Medicine, vol. 334, No. 9, Feb. 29, 1996, pp. 567-572, XP055212321 (6 pages total).

GE Healthcare "TiP-TV™ Training in Partnership Program Supplement and Test for Imaging Professionals—US: Imaging the Gravid Cervix—Helpful Hints", 1.0 ASRT-approved Category A CE Credit, Feb. 2, 2006, 12 pgs. total.

* cited by examiner

ULTRASOUND IMAGE APPARATUS AND METHOD OF OPERATING THE SAME

CROSS-REFERENCE TO RELATED APPLICATION

This application claims the benefit of Korean Patent Application No. 10-2014-0169967, filed on Dec. 1, 2014, in the Korean Intellectual Property Office, the disclosure of which is incorporated herein in its entirety by reference.

BACKGROUND

1. Field

One or more exemplary embodiments relate to an ultrasound imaging apparatus and a method of operating the same, and more particularly, to an ultrasound imaging apparatus configured to display an image generated using ultrasound data of an object and a method of operating the same.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissue or blood flow). In particular, ultrasound diagnosis apparatuses are used for medical purposes including observing an internal area of an object, detecting foreign substances, and assessing injuries. Such ultrasound diagnosis apparatuses provide high stability, display images in real time, and are safe due to no radiation exposure, compared to X-ray apparatuses. Therefore, an ultrasound diagnosis apparatus is widely used together with other types of imaging diagnosis devices.

SUMMARY

One or more exemplary embodiments include an ultrasound imaging apparatus and a method of operating the same, which are capable of extracting a region to be measured by using ultrasound data and providing information about the extracted region.

Additional aspects will be set forth in part in the description which follows and, in part, will be apparent from the description, or may be learned by practice of the presented exemplary embodiments.

According to one or more exemplary embodiments, an ultrasound imaging apparatus includes: a data acquisition unit configured to acquire ultrasound data for an object including a cervix; a controller configured to measure at least one guide line corresponding to the cervix based on the acquired ultrasound data; and a display configured to display measurement information regarding the at least one guide line.

The data acquisition unit acquires ultrasound data including a fetal head region of the object.

The at least one guide line comprises at least one selected from a boundary line of the fetal head region, a boundary line corresponding to a funnel length of the cervix, and a boundary line corresponding to a cervical length of the cervix, all the boundary lines being indicated on an ultrasound image generated based on the ultrasound data.

The measurement information comprises at least one selected from information about a shape of the cervix, a funnel length of the cervix, a cervical length of the cervix, and a histogram corresponding to at least one position included in the cervix.

The controller extracts the fetal head region based on the at least one guide line, extracts a funneling region and the funnel length based on the fetal head region, extracts the cervical length based on at least one of the fetal head region and the funneling region, and determines a shape of the cervix based on at least one of the funnel length and the cervical length.

The controller determines a shape of the cervix based on the at least one guide line, and wherein the display displays a screen depicting the determined shape of the cervix.

The display displays an ultrasound image obtained using the ultrasound data.

The display displays a screen in which the at least one guide line is indicated on the ultrasound image.

A user interface configured to receive an input for editing the at least one guide line indicated on the ultrasound image.

The display displays a schematic diagram corresponding to the determined shape of the cervix on the screen.

The display indicates at least one line corresponding to the at least one guide line on the schematic diagram.

The display displays a histogram corresponding to at least one position included in the first region and indicates the at least one position on the ultrasound image.

The controller determines the shape of the cervix to be a first shape among a plurality of predesignated shapes by using at least one guide line, and
wherein the display displays a screen showing the shape of the cervix determined to be the first shape.

According to one or more exemplary embodiments, a method of operating an ultrasound imaging apparatus comprises: acquiring ultrasound data for an object including a cervix; measuring at least one guide line corresponding to the cervix based on the acquired ultrasound data; and displaying measurement information regarding the at least one guide line.

The method further comprises acquiring ultrasound data including a fetal head region of the object.

The at least one guide line comprises at least one selected from a boundary line of the fetal head region, a boundary line corresponding to a funnel length of the cervix, and a boundary line corresponding to a cervical length of the cervix, all the boundary lines being indicated on an ultrasound image generated based on the ultrasound data.

The displaying of the measurement information, comprises displaying at least one selected from information about a shape of the cervix, a funnel length of the cervix, a cervical length of the cervix, and a histogram corresponding to at least one position included in the cervix.

The method further comprises: determining a shape of the cervix based on the at least one guide line, and displaying a screen depicting the determined shape of the cervix.

The displaying of the screen depicting the determined shape of the cervix comprises displaying at least one selected from a schematic diagram corresponding to the shape of the cervix, an icon corresponding to the shape of the cervix, and a histogram corresponding to at least one position included in the cervix.

The displaying of the screen depicting the determined shape of the cervix comprises indicating at least one line corresponding to the at least one guide line on the schematic diagram.

The method further comprises: displaying a histogram corresponding to at least one position included in the cervix; and indicating the at least one position on an ultrasound image.

The method further comprises displaying an ultrasound image obtained using the ultrasound data.

The displaying of the ultrasound image comprises displaying a screen in which the at least one guide line is indicated on the ultrasound image.

The method further comprises receiving an input for editing the at least one guide line indicated on the ultrasound image.

According to one or more exemplary embodiments, a non-transitory computer-readable recording medium has recorded thereon a program for executing a method of operating an ultrasound imaging apparatus. The method comprises: acquiring ultrasound data for an object including a cervix; measuring at least one guide line corresponding to the cervix based on the acquired ultrasound data; and displaying measurement information regarding the at least one guide line.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
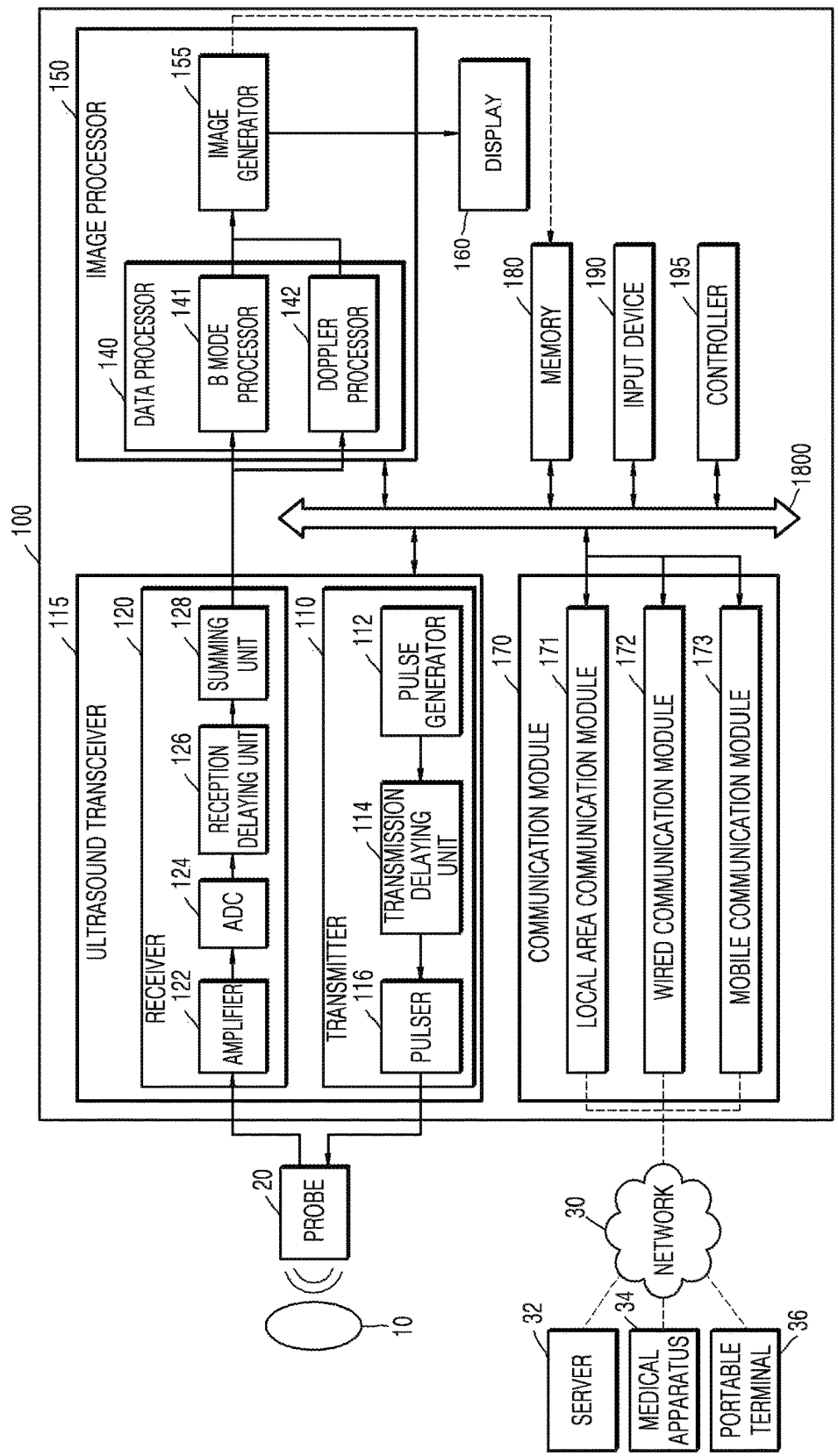
FIG. 1 is a block diagram of a configuration of an ultrasound diagnosis apparatus related to exemplary embodiments.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

It will be understood that, although the terms "first", "second", etc. may be used herein to describe the elements and/or components should not be limited by these terms. These terms are only used to distinguish one element or component from another element or component. Thus, a first element could be termed a second element, and, similarly, a second element could be termed a first element, without departing from the scope of example embodiments. As used herein, the term "and/or" includes any and all combinations of one or more of the associated listed items.

Throughout the specification, an "image" may mean multi-dimensional data formed of discrete image elements, e.g., pixels in a two-dimensional (2D) image and voxels in a three-dimensional (3D) image.

Throughout the specification, an "ultrasound image" refers to an image of an object, which is obtained using ultrasound waves. An ultrasound image may mean an image obtained by transmitting ultrasound signals generated by transducers of a probe to an object and receiving information about echo signals reflected from the object. Furthermore, an ultrasound image may take different forms. For example, the ultrasound image may be at least one selected from an amplitude (A) mode image, a brightness (B) mode image, a color (C) mode image, and a Doppler (D) mode image. In addition, according to an exemplary embodiment, the ultrasound image may be a 2D or 3D image.

Furthermore, an "object" may be a human, an animal, or a part of a human or animal. For example, the object may be an organ (e.g., the liver, the heart, the uterus, the brain, a breast, or the abdomen), or a blood vessel. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Exemplary embodiments will now be described more fully hereinafter with reference to the accompanying drawings so that they may be easily implemented by one of ordinary skill in the art. However, the present embodiments may have different forms and should not be construed as being limited to the descriptions set forth herein. Expressions such as "at least one of," when preceding a list of elements, modify the entire list of elements and do not modify the individual elements of the list.

FIG. 1 is a block diagram of a configuration of an ultrasound diagnosis apparatus 100 related to exemplary embodiments.

Referring to FIG. 1, the ultrasound diagnosis apparatus 100 may include a probe 20, an ultrasound transceiver 115, an image processor 150, a display 160, a communication module 170, a memory 180, a input device 190, and a controller 195, which may be connected to one another via buses 185. Furthermore, the image processor 150 may include an image generator 155, a cross-section information detector 130 (not shown), and the display 160.

It will be understood by those skilled in the art that the ultrasound diagnosis apparatus 100 may further include other common components than those shown in FIG. 1.

In some embodiments, the ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 115 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 100 by wire or wirelessly, and according to embodiments, the ultrasound diagnosis apparatus 100 may include a plurality of probes 20.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 124 by delay times necessary for determining reception directionality, and the summing unit 128 generates ultrasound data by summing the echo signals processed by the reception delaying unit 126.

The image processor 150 generates an ultrasound image by scan-converting ultrasound data generated by the ultrasound transceiver 115.

The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 141 extracts B mode components from ultrasound data and processes the B mode components. The image generator 155 may generate an ultrasound image indicating signal intensities as brightness based on the extracted B mode components.

Similarly, a Doppler processor 142 may extract Doppler components from ultrasound data, and the image generator 155 may generate a Doppler image indicating a movement of an object as colors or waveforms based on the extracted Doppler components.

According to an embodiment, the image generator 155 may generate a three-dimensional (3D) ultrasound image of the object 10 and may also generate an elasticity image by imaging deformation of the object 10 due to pressure. Furthermore, the image generator 155 may display various pieces of additional information in an ultrasound image by using text and graphics. In addition, the generated ultrasound image may be stored in the memory 180.

The display 160 displays the generated ultrasound image. The display 160 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 160 according to embodiments.

The display 160 may include at least one selected from a liquid crystal display (LCD), a thin-film transistor-LCD (TFT-LCD), an organic light-emitting diode (OLED) display, a flexible display, a 3D display, and an electrophoretic display.

Furthermore, when the display 160 and the input device 190 form a layer structure to form a touch screen, the display 160 may be used as an input device as well as an output device, via which a user inputs information via a touch.

The touch screen may be configured to detect a position of a touch input, a touched area, and pressure of a touch. The touch screen may also be configured to detect both an actual touch and a proximity touch.

In the present specification, an 'actual touch' means that a pointer actually touches a screen, and a 'proximity touch' means that a pointer does not actually touch a screen but approaches the screen while being separated from the screen by a predetermined distance. A 'pointer' used herein means a tool for touching a particular portion on or near a displayed screen. Examples of the pointer may include a stylus pen and a body part such as fingers.

Although not shown, the ultrasound diagnosis apparatus 100 may include various sensors that are disposed within or near the touch screen so as to sense an actual touch or proximity touch on the touch screen. A tactile sensor is an example of the sensors for sensing a touch on the touch screen.

The tactile sensor is used to sense a touch of a particular object to the same or greater degree than the degree to which a human can sense the touch. The tactile sensor may detect various pieces of information including the roughness of a contact surface, the hardness of an object to be touched, the temperature of a point to be touched, etc.

A proximity sensor is another example of the sensors for sensing a touch. The proximity sensor refers to a sensor that senses the presence of an object that is approaching or is located near a predetermined detection surface by using the force of an electromagnetic field or infrared light without mechanical contact.

Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, an infrared proximity sensor, and the like.

The communication module 170 is connected to a network 30 by wire or wirelessly to communicate with an external device or a server. The communication module 170 may exchange data with a hospital server or another medical apparatus in a hospital, which is connected thereto via a PACS. Furthermore, the communication module 170 may perform data communication according to the digital imaging and communications in medicine (DICOM) standard.

The communication module 170 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 170 may receive information about a diagnosis history or medical treatment schedule of a patient from a server and utilizes the received information to diagnose the patient. Furthermore, the communication module 170 may perform data communication not only with a server or a medical apparatus in a hospital, but also with a portable terminal of a medical doctor or patient.

The communication module 170 is connected to the network 30 by wire or wirelessly to exchange data with a server 32, a medical apparatus 34, or a portable terminal 36. The communication module 170 may include one or more components for communication with external devices. For example, the communication module 170 may include a local area communication module 171, a wired communication module 172, and a mobile communication module 173.

The local area communication module 171 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 172 refers to a module for communication using electric signals or optical signals. Examples of wired communication techniques according to an embodiment may include communication via a twisted pair cable, a coaxial cable, an optical fiber cable, and an Ethernet cable.

The mobile communication module 173 transmits or receives wireless signals to or from at least one selected from a base station, an external terminal, and a server on a mobile communication network. The wireless signals may be voice call signals, video call signals, or various types of data for transmission and reception of text/multimedia messages.

The memory 180 stores various data processed by the ultrasound diagnosis apparatus 100. For example, the memory 180 may store medical data related to diagnosis of an object, such as ultrasound data and an ultrasound image that are input or output, and may also store algorithms or programs which are to be executed in the ultrasound diagnosis apparatus 100.

The memory 180 may be any of various storage media, e.g., a flash memory, a hard disk drive, EEPROM, etc. Furthermore, the ultrasound diagnosis apparatus 100 may utilize web storage or a cloud server that performs the storage function of the memory 180 online.

The input device 190 generates input data that is input for controlling the operation of the ultrasound diagnosis apparatus 100. The input device 190 may include hardware components, such as a keypad, a mouse, a touch pad, a track ball, and a jog switch. However, embodiments are not limited thereto, and the input device 190 may further include any of various other elements including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

In particular, the input device 190 may also include a touch screen in which a touch pad forms a layer structure with the display 160.

In this case, according to an exemplary embodiment, the ultrasound diagnosis apparatus 100 may display an ultrasound image in a predetermined mode and a control panel for the ultrasound image on a touch screen. The ultrasound diagnosis apparatus 100 may also sense a user's touch gesture performed on an ultrasound image via a touch screen.

The ultrasound diagnosis apparatus 100 may include as physical buttons some buttons that are frequently used by a user among buttons that are included in a control panel of a general ultrasound apparatus, and provide the remaining buttons in the form of a GUI via a touch screen The controller 195 may control all operations of the ultrasound diagnosis apparatus 100. In other words, the controller 195 may control operations among the probe 20, the ultrasound transceiver 100, the image processor 150, the communication module 170, the memory 180, and the input device 190 shown in FIG. 1.

All or some of the probe 20, the ultrasound transceiver 115, the image processor 150, the communication module 170, the memory 180, the input device 190, and the controller 195 may be implemented as software modules. However, embodiments of the present invention are not limited thereto, and some of the components stated above may be implemented as hardware modules. Furthermore, at least one selected from the ultrasound transceiver 115, the image processor 150, and the communication module 170 may be included in the controller 195. However, embodiments of the present invention are not limited thereto.

Figure 2:
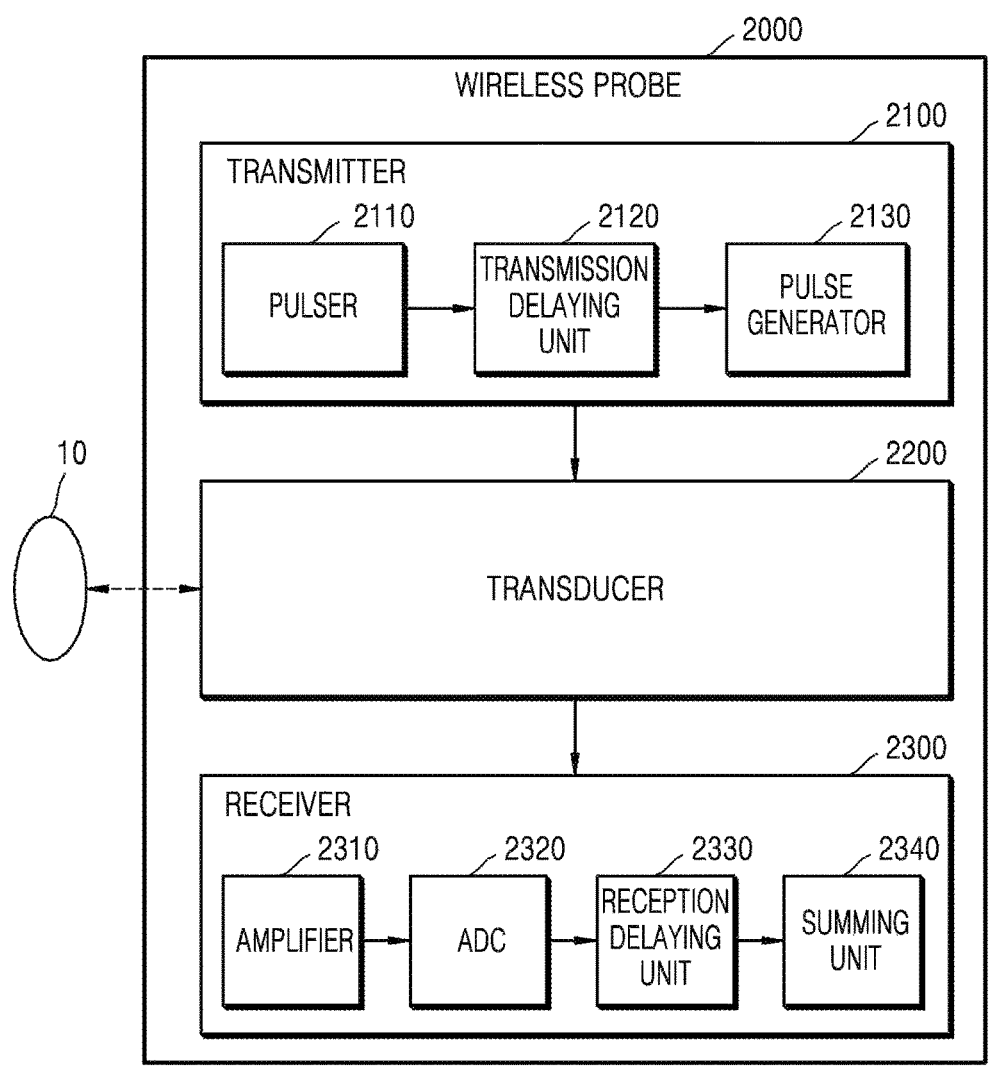
FIG. 2 is a block diagram of a configuration of a wireless probe related to exemplary embodiments, (according to an exemplary embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 100 shown in FIG. 1.

The wireless probe 2000 may be a smart device that includes a transducer array to enable ultrasound scanning. In detail, the wireless probe 2000 is a smart device that scans an object via the transducer array to acquire ultrasound data. The wireless probe 2000 may then produce an ultrasound image by using the acquired ultrasound data and/or display the ultrasound image. The wireless probe 2000 may include a display that displays a screen including at least one ultrasound image and/or a user interface screen for controlling an operation of scanning the object.

While a user scans a certain part of a patient's body by using the wireless probe 2000, the wireless probe 2000 may continuously exchange predetermined data with the ultrasound diagnosis apparatus 100 of FIG. 1 via a wireless network. In detail, while a user scans a certain part of a patient's body by using the wireless probe 2000, the wireless probe 2000 may transmit ultrasound data to the ultrasound diagnosis apparatus 100 in real-time via a wireless network. The ultrasound data may be updated in real-time as the ultrasound scan continues and then be transmitted from the wireless probe 2000 to the ultrasound diagnosis apparatus 100.

Figure 3:
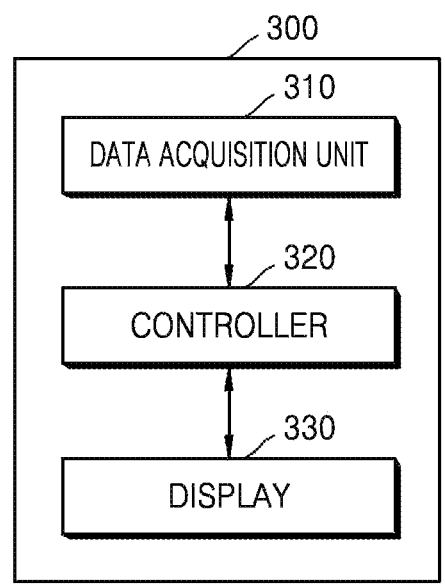
FIG. 3 is a block diagram of a configuration of an ultrasound imaging apparatus according to an exemplary embodiment.

FIG. 3 is a block diagram of a configuration of an ultrasound imaging apparatus 300 according to an exemplary embodiment.

The ultrasound imaging apparatus 300 according to the present exemplary embodiment may include a data acquisition unit 310, a controller 320, and a display 330. However, all of the components shown in FIG. 3 are not essential components. The ultrasound imaging apparatus 300 may include more or fewer components than those shown in FIG. 3. The components will now be described in detail.

The data acquisition unit 310, the controller 320, and the display 330 of the ultrasound imaging apparatus 300 of FIG. 3 may respectively correspond to the image processor 150, the controller 195, and the display 160 of the ultrasound diagnosis apparatus 100 of FIG. 1, and the same descriptions as already presented with respect to FIG. 1 are omitted.

The data acquisition unit 310 acquires ultrasound data for an object including a first region and a second region that is used to determine a shape of the first region. For example, the ultrasound imaging apparatus 300 may further include a probe. When the first and second regions of the object are scanned using the probe, ultrasound data for the object is acquired from the probe. The data acquisition unit 310 acquires the ultrasound data through the probe.

Furthermore, the data acquisition unit 310 may acquire ultrasound data from an external device that is physically independent of the ultrasound imaging apparatus 300, other than via the probe.

In this case, the external device is a device for acquiring, storing, processing, or using data related to an ultrasound image, and may be a medical imaging apparatus, a medical server, a portable terminal, or any other computing device that uses and processes a medical image. For example, the external device may be a medical diagnosis apparatus used in a medical institution such as a hospital. Furthermore, the external device may be a server in a hospital for recording and storing a patient's clinical history, a medical imaging apparatus used by a medical doctor in a hospital to read a medical image, or the like.

An object may be a human (e.g., a pregnant woman), a first region may be the cervix, and a second region may be a fetal head region that is near the cervix. The ultrasound imaging apparatus 300 provides an ultrasound image based on ultrasound data. A medical doctor may determine the status of a pregnant woman's uterus by examining an ultrasound image. The pregnant woman has the risk of preterm delivery due to cervical incompetence or a short cervical length (CL). The medical doctor may determine cervical incompetence based on at least one of a CL, a cervical shape, and a histogram of a region around_ a cervix. The ultrasound imaging apparatus 300 may provide information about at least one selected from a CL, a cervical shape, and a histogram of a region around a cervix. In this way, the ultrasound imaging apparatus 300 allows the medical doctor to objectively determine the status of a pregnant woman's uterus by providing information related to the cervix.

The controller 320 extracts the second region of the object from ultrasound data. The controller 320 sets at least one guide line corresponding to the first region based on the second region. The controller 320 controls the at least one guide line to be measured. In this case, to do so, the controller 320 may measure a guide line itself or a line corresponding to the guide line. The controller 320 then determines a shape of the first region based on the measured at least one guide line.

If the first region is the cervix of the object (or the cervix of a pregnant woman), and the second region is a fetal head region that is near the cervix, the controller 320 determines a shape of the cervix based on at least one guide line. In this case, the at least one guide line includes at least one of a boundary line of the fetal head region, a boundary line corresponding to a funnel length of the cervix, and a boundary line corresponding to a CL of the cervix, all the boundary lines being indicated on an ultrasound image generated based on ultrasound data, but is not limited thereto. A funnel length is used to determine a shape of the cervix. Information about a funneling region may include a funnel length and a funnel width. The funneling region may have a form of a funnel The funnel length is a dimension of the funneling region corresponding to a height of a funnel, and the funnel width is a dimension corresponding to a diameter of the funnel. The funneling region will be described in more detail below with reference to FIG. 5.

The controller 320 first extracts the fetal head region based on ultrasound data. The controller 320 also extracts a funneling region and a funnel length based on the fetal head region. The controller 320 then measures a CL based on at least one of the fetal head region and the funneling region. The controller 320 also determines a shape of a uterus based on at least one of the funnel length and the CL. In this case, when ultrasound data is acquired by the data acquisition unit 310, the controller 320 may automatically perform a process_up to an operation of determining the shape of the uterus by using the ultrasound data. Alternatively, the controller 320 may perform the process by receiving a user input at each operation of the process.

The controller 320 controls the display 330 to display a predetermined screen. The display 330 may display the predetermined screen so that a user or patient may visually recognize a predetermined image or information. The display 330 may correspond to the display 160 of the ultrasound diagnosis apparatus 100 of FIG. 1, or have a different configuration than that of the display 160 thereof.

The display 330 displays a predetermined screen. In detail, the display 330 displays the predetermined screen according to control by the controller 320. The display 330 includes a display panel (not shown) and may display a user interface screen, a medical image screen, etc., on the display panel.

The display 330 displays measurement information regarding at least one guide line. In this case, the measurement information may include a length of the at least one guide line or of a line corresponding to the at least one guide line. A length of a guide line or a line corresponding to the guide line may be used to determine a shape of a first region. In detail, the measurement information may include at least one of information about a shape of a cervix, a funnel length of the cervix, a CL of the cervix, and a histogram corresponding to at least one position included in the cervix.

The controller 320 may determine a shape of the first region to be a first shape among a plurality of predesignated shapes by using at least one guide line. The display 330 displays a screen depicting the shape of the first region. In detail, the display 330 may display a schematic diagram corresponding to the shape of the first region on the screen.

For example, if the first region is a cervix of an object and the second region is a fetal head region that is near the cervix, the controller 320 determines a shape of the cervix based on at least one guide line. A plurality of predesignated shapes representing the shape of the cervix may include "T" type, "V" type, "Y" type, and "U" type shapes, but are not limited thereto. The display 330 may display a schematic diagram corresponding to one of the "T" type, "V" type, "Y" type, and "U" type on the screen.

The display 330 may also display at least one line corresponding to the at least one guide line in the schematic diagram. For example, if the shape of the first region is a "T" type, the display 330 may display a screen in which a T-shaped line is overlaid on the schematic diagram. In this way, the display 330 may provide a screen in which at least one line corresponding to at least one guide line is indicated on the schematic diagram, thereby allowing a user such as a medical doctor or a patient to more easily identify the shape of the first region.

Furthermore, the display 330 may display at least one of a schematic diagram and an icon, both of which correspond to a shape of the first region. For example, if the first region is a cervix, the display 330 may display at least one of a schematic diagram and an icon, both corresponding to a shape of the cervix. The display 330 may provide information about the shape of the first region by displaying one of a plurality of icons distinctly from the other ones. For example, the display 330 may display a contour of one of a plurality of icons corresponding to a shape of the first region as a dashed line and contours of the other icons as solid lines so as to distinguish the icon corresponding to the shape of the first region from the other ones.

The display 330 displays an ultrasound image obtained using ultrasound data. The display 330 may also display a screen in which at least one guide line is indicated on the ultrasound image. Furthermore, the display 330 may display at least one guide line in a layout that is different from a layout of the ultrasound image. By displaying the at least one guide line in a layout that is different from the layout of the ultrasound image, it is possible to keep the original ultrasound image intact and modify the at least one guide line.

The display 330 also displays a histogram corresponding to at least one position included in the first region. Furthermore, the display 330 may indicate which position in the first region corresponds to the histogram by displaying the at least one position on an ultrasound image.

The ultrasound imaging apparatus 300 includes a central arithmetic processor to control overall operations of the data acquisition unit 310, the controller 320, and the display 330. The central arithmetic processor may be implemented by an array of a plurality of logic gates or by a combination of a general-purpose microprocessor and a memory for storing a program to be executed on the general-purpose microprocessor. It will also be understood by one of ordinary skill in the art that the central arithmetic processor may be implemented using other types of hardware.

Hereinafter, various operations performed by an ultrasound imaging apparatus and applications thereof will be described in detail. Although none the data acquisition unit 310, the controller 320, and the display 330 are specified, one of ordinary skill in the art may easily understand their features and aspects. The scope of the present inventive concept is not limited by a name of a particular component or physical/logical structure.

Figure 4:
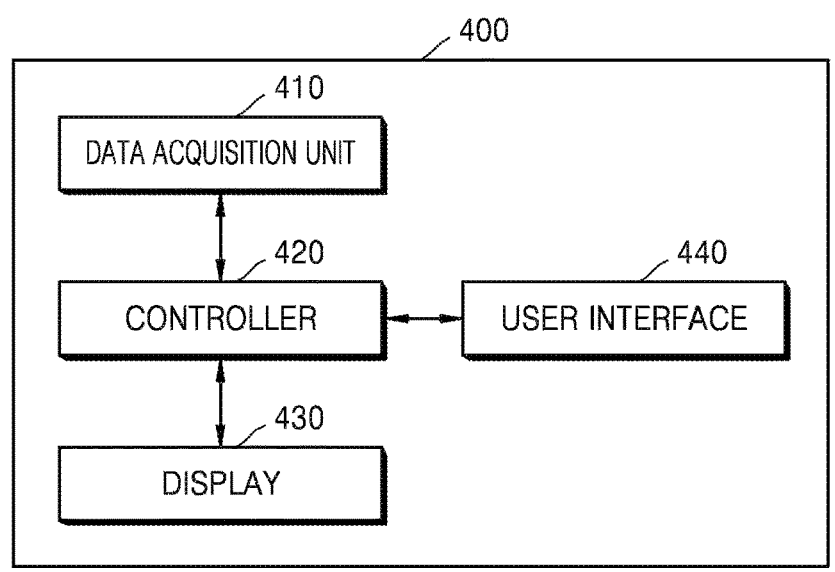
FIG. 4 is a block diagram of a configuration of an ultrasound imaging apparatus according to another exemplary embodiment.

FIG. 4 is a block diagram of a configuration of an ultrasound imaging apparatus 400 according to another exemplary embodiment. The ultrasound imaging apparatus 400 of FIG. 4 may further include a user interface 440, in comparison to the ultrasound imaging apparatus 300 of FIG. 3.

Since a data acquisition unit 410, a controller 420, and a display 430 in the ultrasound imaging apparatus 400 of FIG. 4 respectively correspond to the data acquisition unit 310, the controller 320, and the display 330 in the ultrasound imaging apparatus 300 of FIG. 3, the same descriptions as already presented with respect to FIG. 3 are omitted.

The display 430 displays an ultrasound image generated using ultrasound data. The controller 420 extracts a second region from the ultrasound data for an object including a first region and the second region and sets at least one guide line corresponding to the first region based on the second region. The display 430 displays the at least one guide line on the ultrasound image obtained from the ultrasound data. In other words, the display 430 may receive information about the at least one guide line that is used to determine a shape of the first region to thereby indicate the at least one guide line on the ultrasound image.

Furthermore, the display 430 may receive information about at least one guide line from the user interface 440 to indicate the at least one guide line on an ultrasound image. In this case, the user may directly indicate at least one guide line via the user interface 440.

Furthermore, if at least one guide line used to determine a shape of the first region is indicated on an ultrasound image, the user interface 440 may receive an input for editing the at least one guide line indicated on the ultrasound image.

The user interface 440 refers to a device via which data for controlling the ultrasound imaging apparatus 400 is received from the user. The user interface 440 may include hardware components such as a keypad, a mouse, a touch panel, a touch screen, a trackball, a jog switch, etc. However, exemplary embodiments are not limited thereto, and the user interface 440 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The user interface 440 may generate and output a user interface screen for receiving a predetermined command or data from the user. The user interface 440 may also receive the predetermined command or data from the user via the user interface screen. The user may view the user interface screen displayed via the display 430 to recognize predetermined information and input a predetermined command or data via the user interface 440.

For example, the user interface 440 may be formed as a touch pad. In detail, the user interface 440 includes a touch pad (not shown) combined with a display panel (not shown) in the display 430 and outputs a user interface screen to the display panel. When a predetermined command is input via the user interface screen, the touch pad may detect information about the predetermined command and then transmit the detected information to the controller 420. Then, the controller 420 may interpret the detected information to recognize and execute the predetermined command input by the user.

The ultrasound imaging apparatus 400 may further include a storage unit (not shown) and a communication module (not shown). The storage unit may store data related to an ultrasound image (e.g., the ultrasound image, ultrasound data, scan-related data, data related to diagnosis of a patient, etc.), data transmitted from an external device to the ultrasound imaging apparatus 400, etc. The data transmitted from the external device may include patient-related information, data necessary for diagnosis and treatment of a patient, a patient's past medical history, a medical work list corresponding to instructions regarding diagnosis of a patient, and the like.

The communication module may receive and/or transmit data from and/or to an external device. For example, the communication module may connect to a wireless probe or an external device via a communication network based on Wi-Fi or Wi-Fi Direct (WFD) technology. In detail, examples of a wireless communication network to which the communication module can connect may include, but are not limited to, Wireless LAN (WLAN), Wi-Fi, Bluetooth, ZigBee, WFD, Ultra Wideband (UWB), Infrared Data Association (IrDA), Bluetooth Low Energy (BLE), and Near Field Communication (NFC).

Figure 5:
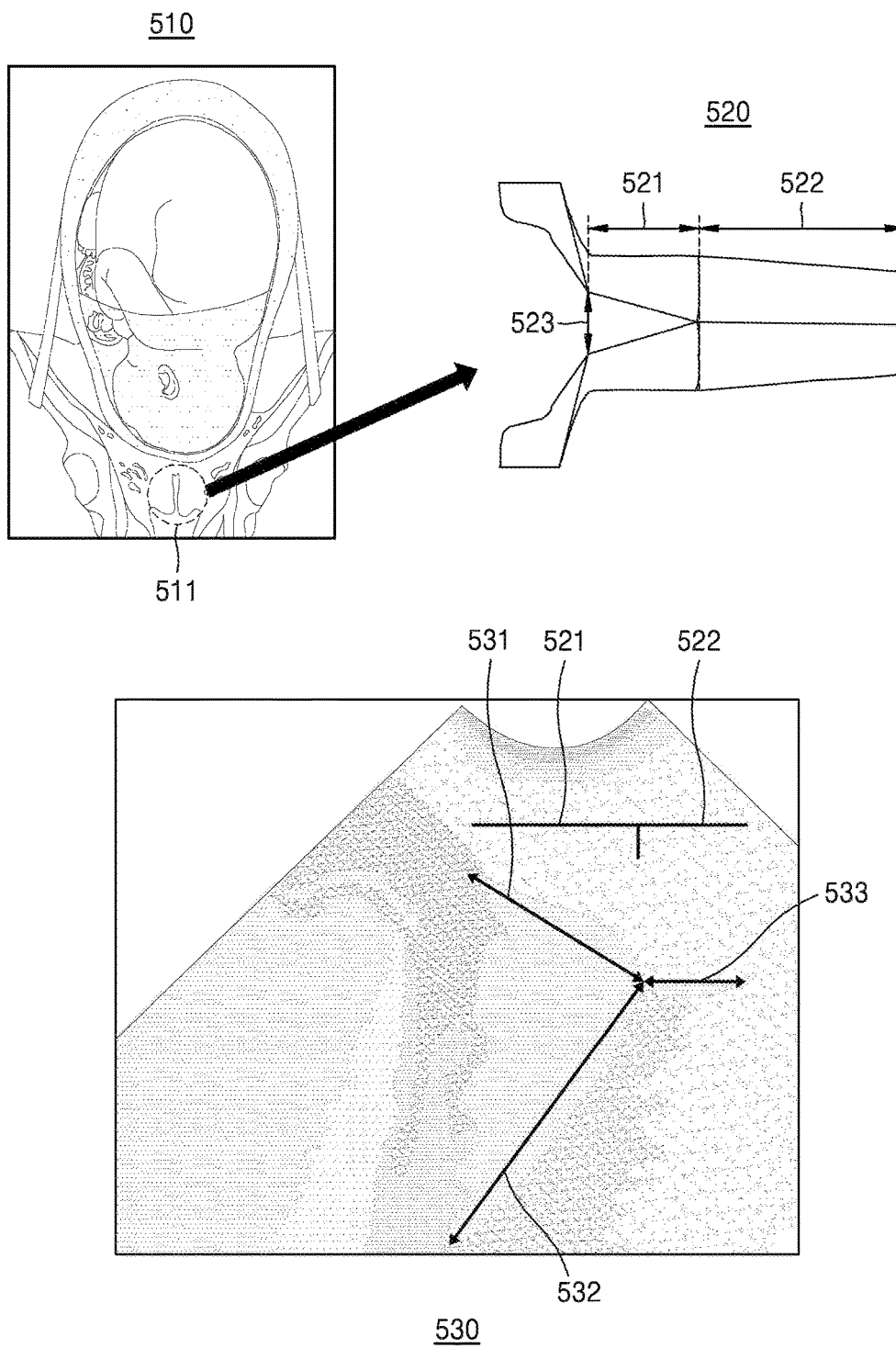
FIG. 5 is a diagram for explaining a guide line corresponding to a cervix according to an exemplary embodiment.

FIG. 5 is a diagram for explaining a guide line corresponding to a cervix 511, according to an exemplary embodiment.

Referring to 510 of FIG. 5, during pregnancy, a fetal head region is located near the cervix 511. As a pregnant woman approaches the time of birth, a CL decreases. Thus, the time of birth may be estimated based on a length and a shape of a pregnant woman's cervix, a histogram of a region near a cervix, etc.

Referring to 520 of FIG. 5, the cervix 511 may be made up of a funneling region and a cervical region. Information about the funneling region may be represented by a funnel length 521 and a funnel width 523. Information about the cervical region may be represented by a CL 522. Furthermore, the status and shape of the cervix 511 may be determined based on information about funneling. The percentage of funneling is defined by Equation (1) below:

$$\text{Percentage of Funneling} = \text{funnel length}/\text{CL} + \text{funnel length} \times 100\% \quad (1)$$

Cervical funneling is correlated with the status of a pregnant woman's cervix. A large percentage of funneling indicates that the time of birth is approaching. The ultrasound imaging apparatus 300 of FIG. 3 may determine a shape of the uterus based on funneling. For example, if the percentage of funneling is 20%, the shape of the uterus may be determined to be 'V' type. If the percentage of funneling is 100%, the shape of the uterus may be determined to be a 'U' type.

Although a funnel width is not used in Equation (1), the funnel width may also be used to determine the shape of the uterus. As the time of birth approaches, the funnel width increases.

Referring to 530 of FIG. 5, the ultrasound imaging apparatus 300 displays an ultrasound image of a pregnant woman's uterus. The ultrasound imaging apparatus 300 may indicate guide lines 531 and 532 corresponding to the funnel length 521 and a guide line 533 corresponding to the CL 522 on the ultrasound image. The ultrasound imaging apparatus 300 then determines a shape of the cervix 511 based on the guide lines 531 through 533 and displays measurement information regarding the guide lines 531 through 533.

Figure 6:
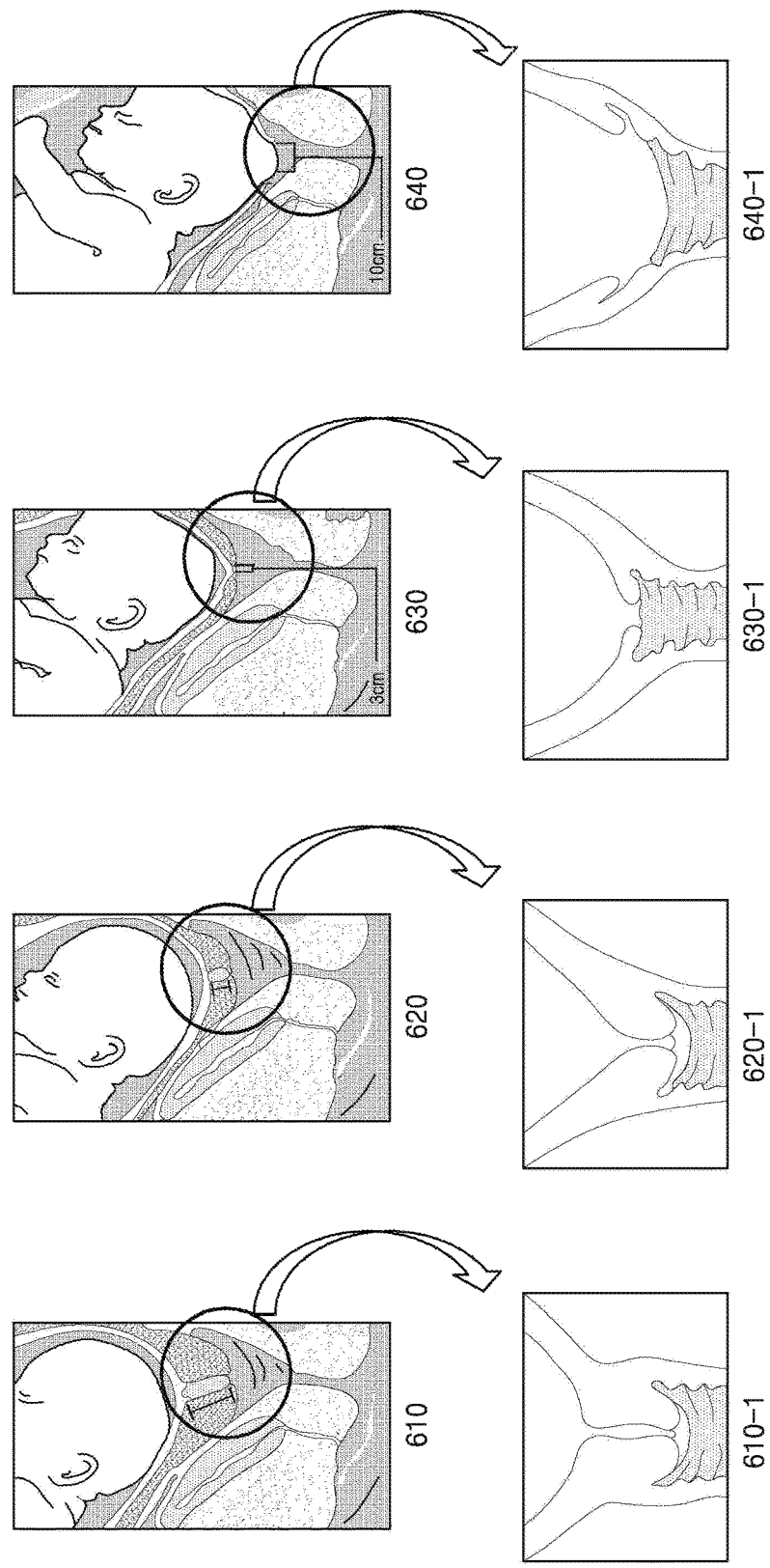
FIG. 6 is a diagram for explaining a change in a cervix according to stages of pregnancy, according to an exemplary embodiment.

FIG. 6 is a diagram for explaining a change in a cervix according to stages of pregnancy, according to an exemplary embodiment. Referring to FIG. 6, a position of a fetal head region and a CL vary depending on stages of pregnancy.

Referring to 610 of FIG. 6, in the first trimester of pregnancy, the fetal head region is located near a cervix, and the cervix remains closed. As seen on a cervix 610-1 in detail, the funnel width 523 has not changed since the pregnant woman's cervix has not opened. Thus, the shape of the cervix 610-1 may be classified as a "T" type. In this case, the percentage of funneling may be 0%.

Referring to 620, during the second trimester of pregnancy, the fetal head region is located closer to the cervix than in the first trimester, and the cervix remains slightly open. As seen on a cervix 620-1 in detail, the funnel width 523 becomes greater than the funnel width 523 during the first trimester. The shape of the cervix 620-1 may be classified as a "V" shape, and the percentage of funneling may be 30%. In this case, 30% is merely an exemplary value, and it will be understood by one of ordinary skill in the art that the percentage of funneling may have another value.

Referring to 630, during the third trimester of pregnancy, since the time of birth is pending, the cervix is opened wider than during the second trimester of pregnancy. The shape of the cervix may be classified as a "Y" type, and the percentage of funneling may be 100%. In this case, 100% is merely an exemplary value, and it will be understood by one of ordinary skill in the art that the percentage of funneling may have another value.

Referring to 640, since the pregnant woman is about to give birth to a baby, the cervix remains open wider than during the third trimester of pregnancy. As seen on a cervix 640-1 in detail, the cervix 640-1 remains open so that the baby' head is pushed out through the cervix. In this case, the shape of the cervix 640-1 may be classified as a "U" type.

FIGS. 7 through 10 are diagrams for explaining shapes of a cervix by analyzing guide lines on an ultrasound image, according to exemplary embodiments.

Figure 7:
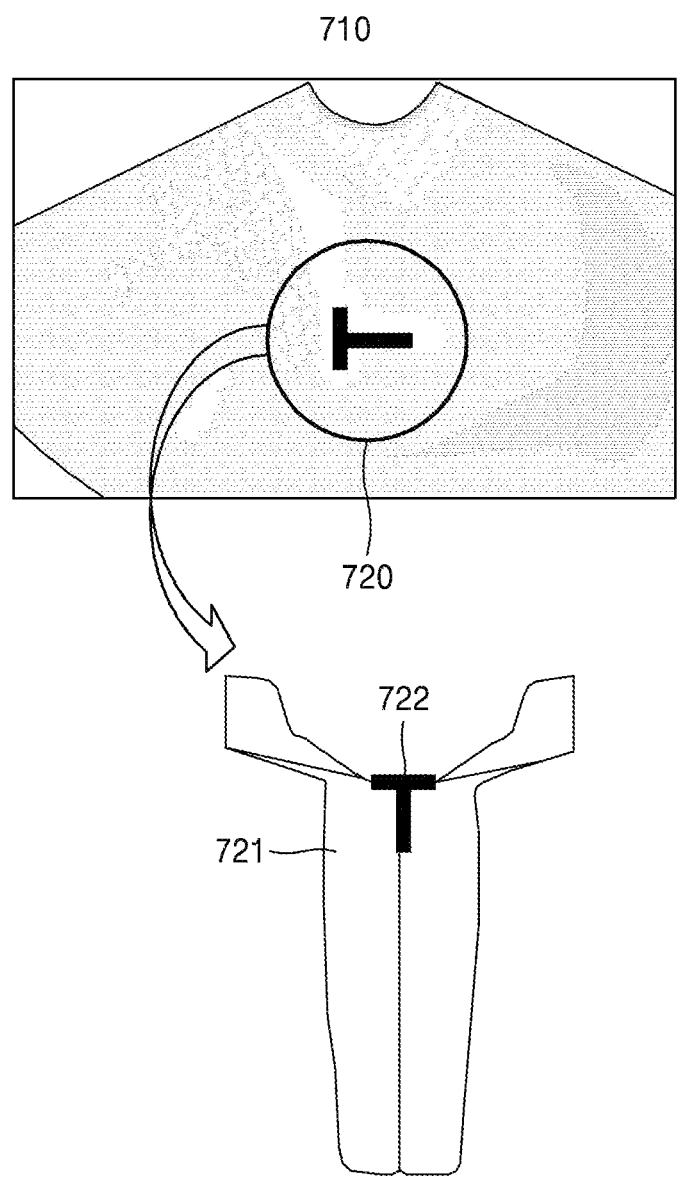
FIGS. 7 through 10 are diagrams for explaining shapes of a cervix by analyzing guide lines on an ultrasound image, according to exemplary embodiment.

FIG. 7 is a diagram for explaining a shape of a cervix by analyzing a guide line on an ultrasound image according to an exemplary embodiment. The ultrasound imaging apparatus 300 of FIG. 3 may display an ultrasound image obtained using ultrasound data for a pregnant woman. The ultrasound data may include data related to the cervix and a fetal head region that is near the cervix. Referring to 710 of FIG. 7, the ultrasound imaging apparatus 300 may extract a fetal head region based on the ultrasound data. The ultrasound imaging apparatus 300 may extract a funneling region by indicating a tangent line in the fetal head region. The funneling region may be included in the cervix, and information about the funneling region may be represented by the funnel length (521 of FIG. 5) and the funnel width (523 of FIG. 5).

Since the cervix is shaped like a "T" shape, as shown in 710, the ultrasound imaging apparatus 300 may determine a shape 720 of the cervix as a "T" type. The ultrasound imaging apparatus 300 may display a T-type schematic diagram 721 representing the shape 720 of the cervix, as shown in FIG. 7 (. The ultrasound imaging apparatus 300 may indicate a line corresponding to the "T" type on the ultrasound image. Furthermore, the ultrasound imaging apparatus 300 may create a screen in which a T-shaped line 722 is indicated on the T-type schematic diagram 721 and display the screen. The ultrasound imaging apparatus 300 may also create a screen including the ultrasound image of the pregnant woman, the T-type schematic diagram 721 of the cervix, and an icon corresponding to the "T" type and display the screen.

Figure 8:
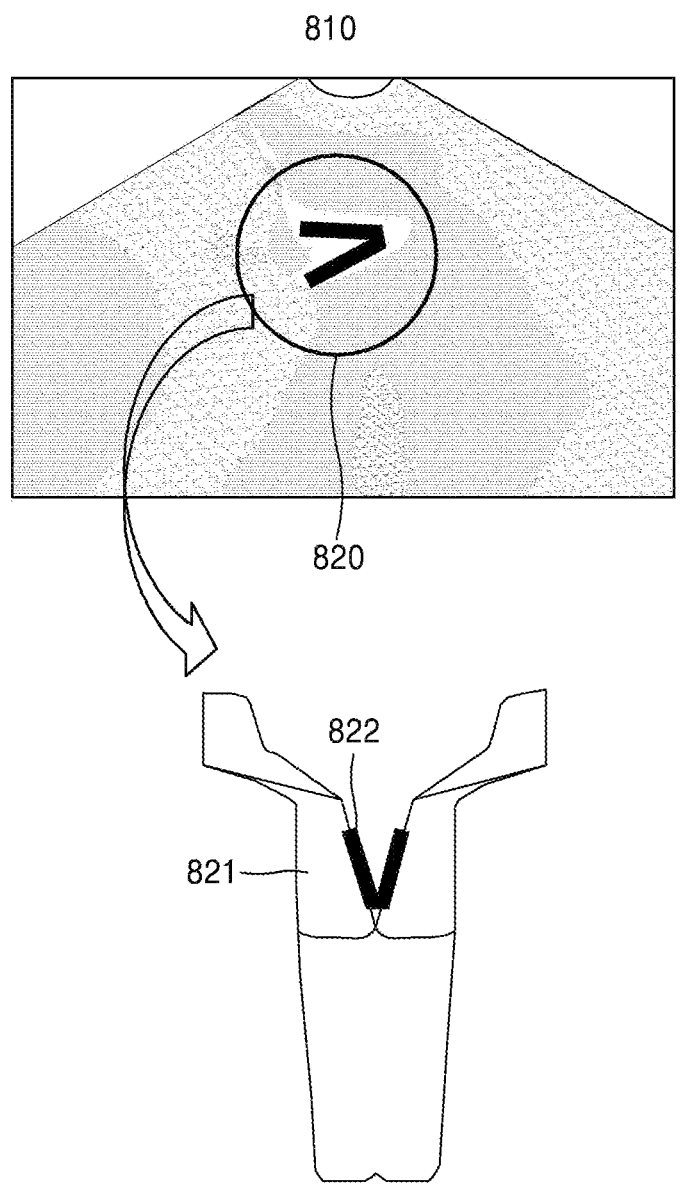

FIG. 8 is a diagram for explaining a shape of a cervix by analyzing a guide line on an ultrasound image of a pregnant woman, according to an exemplary embodiment. Referring to 810 of FIG. 8, the ultrasound imaging apparatus 300 may extract a fetal head region based on ultrasound data. The ultrasound imaging apparatus 300 may indicate on the ultrasound image a boundary line of the fetal head region, a boundary line corresponding to the funnel length (521 of FIG. 5) of the cervix, and a boundary line corresponding to the CL (522 of FIG. 5) of the cervix. Since the cervix is shaped like a "V" shape as shown in 810, the ultrasound imaging apparatus 300 may determine a shape 820 of the cervix as a "V" type. The ultrasound imaging apparatus 300 may display a V-type schematic diagram 821 representing the shape 820 of the cervix, as shown in FIG. 8. The ultrasound imaging apparatus 300 may indicate a line corresponding to the "V" type on the ultrasound image. Furthermore, the ultrasound imaging apparatus 300 may create a screen in which a V-shaped line 822 is indicated on the V-type schematic diagram 821 and display the screen. The ultrasound imaging apparatus 300 may also create a screen including the ultrasound image of the pregnant woman, the V-type schematic diagram 821 of the cervix, and an icon corresponding to the "V" type and display the screen.

Figure 9:
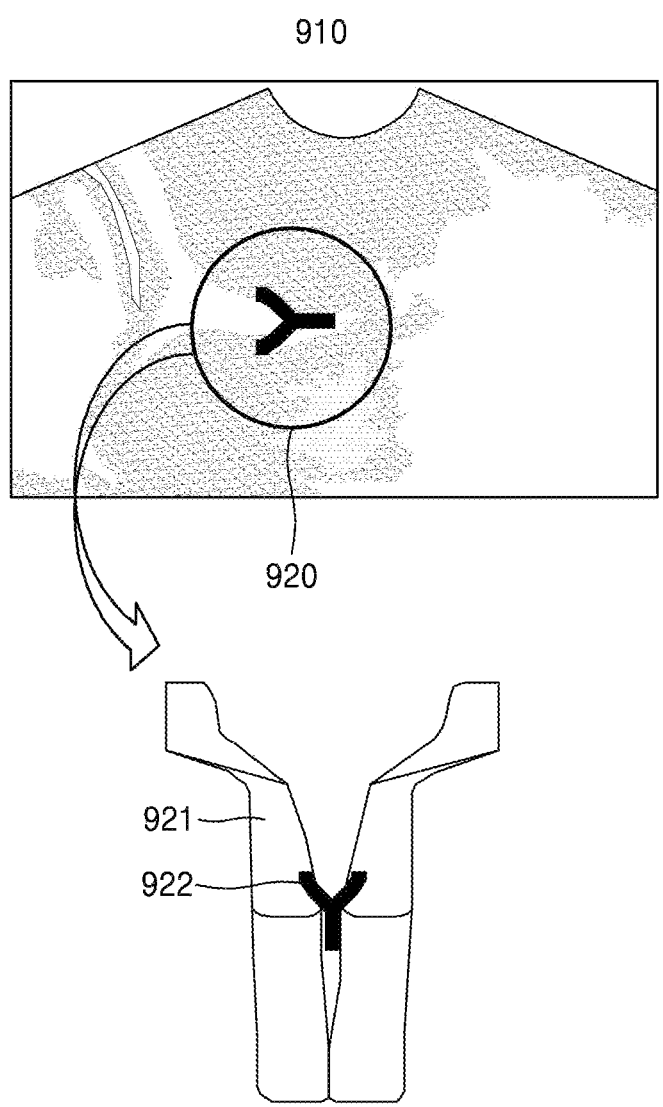

FIG. 9 is a diagram for explaining a shape of a cervix by analyzing a guide line on an ultrasound image of a pregnant woman, according to an exemplary embodiment. Referring to 910 of FIG. 9, the ultrasound imaging apparatus 300 may indicate on the ultrasound image a boundary line corresponding to the funnel length (521 of FIG. 5) of a cervix and a boundary line corresponding to the CL (522 of FIG. 5) of the cervix. Since the cervix is shaped like a "Y" shape as shown in 910, the ultrasound imaging apparatus 300 may determine a shape 920 of the cervix as a "Y" type. The ultrasound imaging apparatus 300 may display a Y-type schematic diagram 921 representing the shape 920 of the cervix as shown in FIG. 9. The ultrasound imaging apparatus 300 may indicate a line corresponding to the "Y" type on the ultrasound image. Furthermore, the ultrasound imaging apparatus 300 may create a screen in which a Y-shaped line 922 is indicated on the Y-type schematic diagram 921 and display the screen. The ultrasound imaging apparatus 300 may also create a screen including the ultrasound image of the pregnant woman, the V-type schematic diagram 921 of the cervix, and an icon corresponding to the "Y" type and display the screen.

Figure 10:
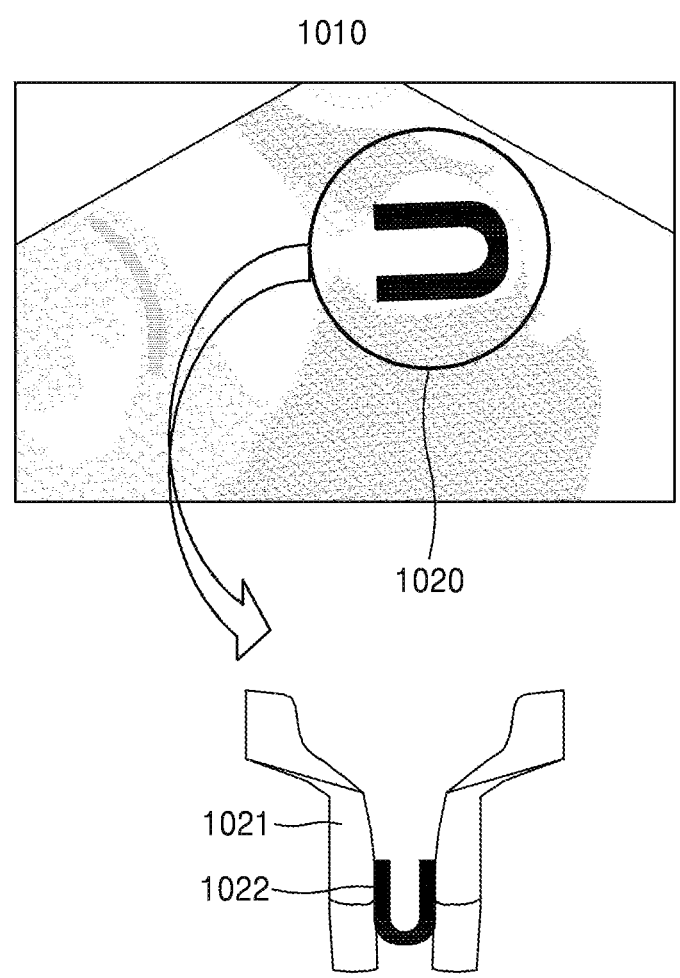

FIG. 10 is a diagram for explaining a shape of a cervix by analyzing a guide line on an ultrasound image of a pregnant woman, according to an exemplary embodiment. Referring to 1010 of FIG. 10, the ultrasound imaging apparatus 300 may indicate a line corresponding to a shape 1020 of the cervix on the ultrasound image. Since the cervix is shaped like a "U" shape, as shown in 1010, the ultrasound imaging apparatus 300 may determine the shape 1020 of the cervix as a "U" type. The ultrasound imaging apparatus 300 may display a U-type schematic diagram 1021 representing the shape 1020 of the cervix as shown in FIG. 10. The ultrasound imaging apparatus 300 may indicate a line corresponding to the "U" type on the ultrasound image. Furthermore, the ultrasound imaging apparatus 300 may create a screen in which a U-shaped line 1022 is indicated on the U-type schematic diagram 1021 and display the screen. The ultrasound imaging apparatus 300 may also create a screen including the ultrasound image of the pregnant woman, the U-type schematic diagram 1021 of the cervix, and an icon corresponding to the "U" type and display the screen.

Figure 11:
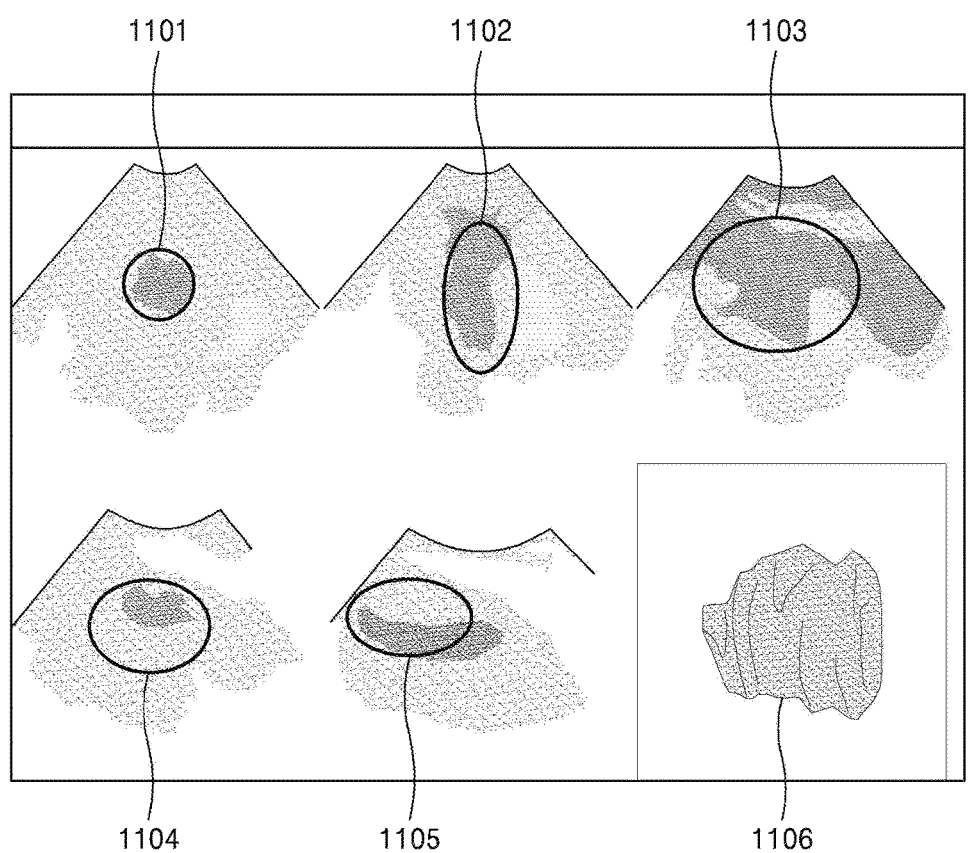
FIG. 11 is a diagram for explaining a screen for providing volume information by using an ultrasound image, according to an exemplary embodiment.

FIG. 11 is a diagram for explaining a screen for providing volume information by using an ultrasound image, according to an exemplary embodiment.

The ultrasound imaging apparatus 300 of FIG. 3 may determine a shape of a first region of an object by using volume information regarding the first region. The ultrasound imaging apparatus 300 may obtain volume information regarding the object based on ultrasound images 1101 through 1105 acquired using ultrasound data. The ultrasound imaging apparatus 300 may then output the first region of the object as a 3D image 1106 by using the volume information regarding the first region.

The ultrasound imaging apparatus 300 may obtain a plurality of pieces of volume information regarding a first region according to the stage of pregnancy (e.g., gestational age of pregnancy) or shape of the first region from each of a plurality of objects. In this case, the ultrasound imaging apparatus 300 may obtain volume information regarding the first region from each of the plurality of objects as well as from an external device. The external device may be an ultrasound diagnosis apparatus or a storage device. The storage device may be any of various storage media such as a hard disk drive (HDD), Read Only Memory (ROM), Random Access Memory (RAM), a flash memory, and a memory card.

The ultrasound imaging apparatus 300 may classify the pieces of volume information regarding the first region according to the stage of pregnancy or shape of the first region and the compare volume information regarding a first region of an object with the classified pieces of volume information regarding the first region. According to a comparison result, the ultrasound imaging apparatus 300 may determine at least one of a shape and a status of the first region of the object.

Figure 12:
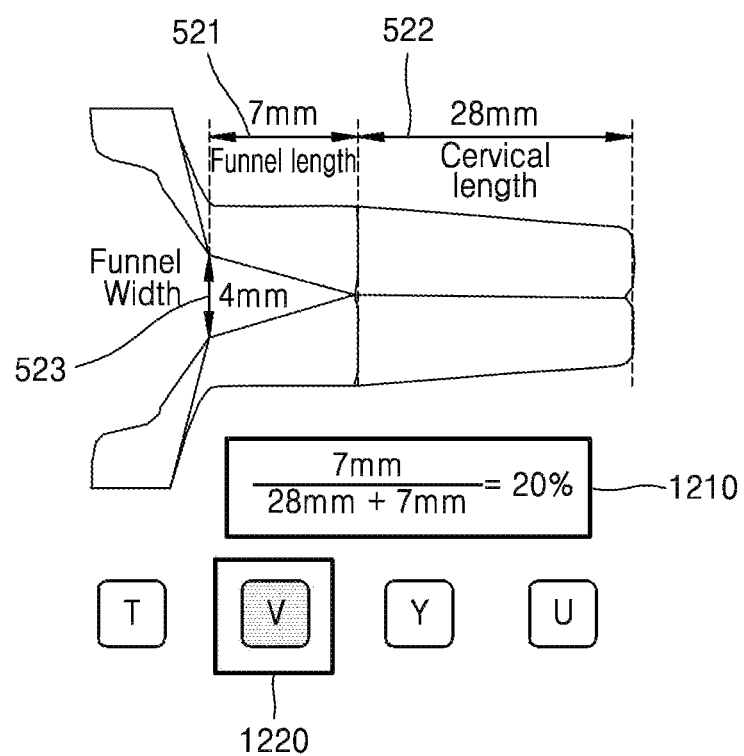
FIGS. 12 through 14 are diagrams for explaining screens that provide information about a cervix according to exemplary embodiment.
Figure 13:
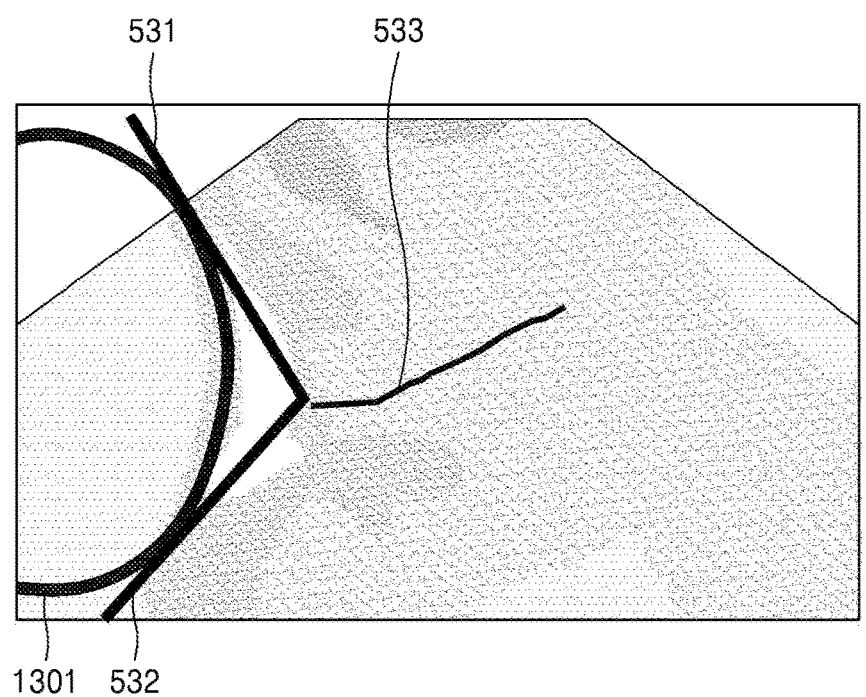
Figure 14:
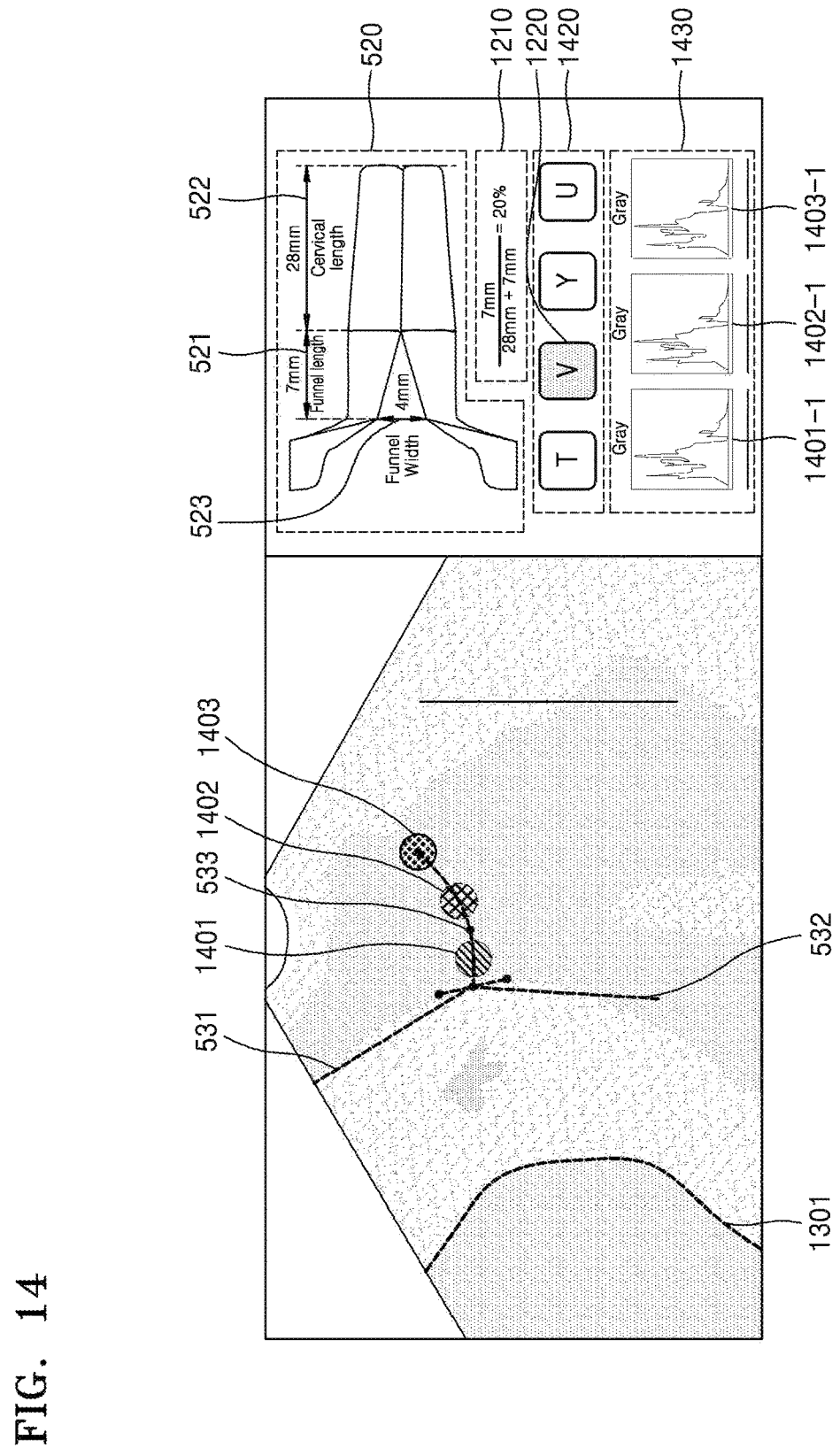

FIGS. 12 through 14 are diagrams for explaining screens that provide information about a cervix according to exemplary embodiments.

Referring to FIG. 12, the ultrasound imaging apparatus 300 displays a screen including a schematic diagram corresponding to a shape of a cervix and an icon 1220 corresponding thereto. The ultrasound imaging apparatus 300 may indicate information about a funnel length 521, a CL 522, and a funnel width 523 on the schematic diagram. The ultrasound imaging apparatus 300 also displays the percentage 1210 of funneling calculated using the funnel length 521 and the CL 522. The ultrasound imaging apparatus 300 displays a plurality of icons so as to distinguish the icon 1220 corresponding to the determined shape of the cervix from the other icons. For example, to do so, the ultrasound imaging apparatus 300 may emphasize a contour of the icon 1220 by thickening the contour thereof.

Referring to FIG. 13, the ultrasound imaging apparatus 300 displays at least one guide line 531 through 533 on an ultrasound image. In detail, the ultrasound imaging apparatus 300 extracts a fetal head region based on ultrasound data and indicates a boundary line 1301 representing the fetal head region on the ultrasound image. The ultrasound imaging apparatus 300 then extracts a funneling region and the funnel length (521 of FIG. 12) based on the fetal head region. To extract the funneling region, the ultrasound imaging apparatus 300 indicates tangent lines to the boundary line 1301 of the fetal head region and determines the funneling region based on the indicated tangent lines. The ultrasound imaging apparatus 300 then extracts the CL (522 of FIG. 12) based on at least one of the fetal head region and the funneling region. The ultrasound imaging apparatus 300 displays the guide lines 531 and 532 corresponding to the funnel length 521 and the guide line 533 corresponding to the CL 522.

Referring to FIG. 14, the ultrasound imaging apparatus 300 displays an ultrasound image of first and second regions of an object, a schematic diagram 520 corresponding to a shape of the first region, measurement information regarding the shape of the first region, an icon 1220 corresponding to the shape of the first region among a plurality of icons 1420, and a plurality of histograms 1430 (1401-1, 1402-1, and 1403-1) respectively corresponding to at least one position 1401 through 1403 included in the first region.

The ultrasound imaging apparatus 300 may create a screen including at least one of the schematic diagram 520 corresponding to the shape of the first region, measurement information regarding the shape of the first region, the icon 1220 corresponding to the shape of the first region among the plurality of icons 1420, and the plurality of histograms 1430 (1401-1, 1402-1, and 1403-1) respectively corresponding to the at least one position 1401 through 1403 included in the first region and display the screen.

In detail, it is assumed herein that the first region is the cervix, and the second region is a fetal head region that is near the cervix. The ultrasound imaging apparatus 300 sets at least one guide line 531 through 533 based on ultrasound data. In this case, the at least one guide line 531 through 533 includes a boundary line 1301 of the fetal head region, the guide lines 531 and 532 corresponding to a funnel length 521 of the cervix, and the guide line 533 corresponding to a CL 522 of the cervix, but is not limited thereto.

The ultrasound imaging apparatus 300 determines a shape of the cervix based on the at least one guide line 531 through 533. For example, the shape of the cervix may be classified as one of a "T" type, a "V" type, a "Y" type, and a "U" type. The ultrasound imaging apparatus 300 creates a screen including information related to the determined shape of the cervix based on the shape of the cervix and displays the screen. The ultrasound imaging apparatus 300 indicates the at least one guide line 531 through 533 that is used to determine the shape of the cervix on the ultrasound image.

The ultrasound imaging apparatus 300 also displays the schematic diagram 520 corresponding to the shape of the cervix. In this case, the ultrasound imaging apparatus 300 may indicate information about a funnel length 521, a CL 522, and a funnel width 523 on the schematic diagram 520. Measurement information regarding the shape of the cervix includes the percentage 1210 of funneling calculated using the funnel length 521 and the CL 522. The ultrasound imaging apparatus 300 displays the calculated percentage 1210 of funneling.

The ultrasound imaging apparatus 300 displays the icon 1220 corresponding to the shape of the cervix in such a manner as to distinguish the icon 1220 from icons 1420 corresponding to a plurality of shapes.

The ultrasound imaging apparatus 300 may display the plurality of histograms 1401-1, 1402-1, and 1403-1 respectively corresponding to the at least one position 1401 through 1403 included in the cervix and indicate the at least one position 1401 through 1403 on the ultrasound image. If the plurality of histograms 1401-1, 1402-1, and 1403-1 are provided, the ultrasound imaging apparatus 300 may display the histograms 1401-1, 1402-1, and 1403-1 respectively corresponding to the at least one position 1401 through 1403 in such a manner as to distinguish them from one another.

Figure 15:
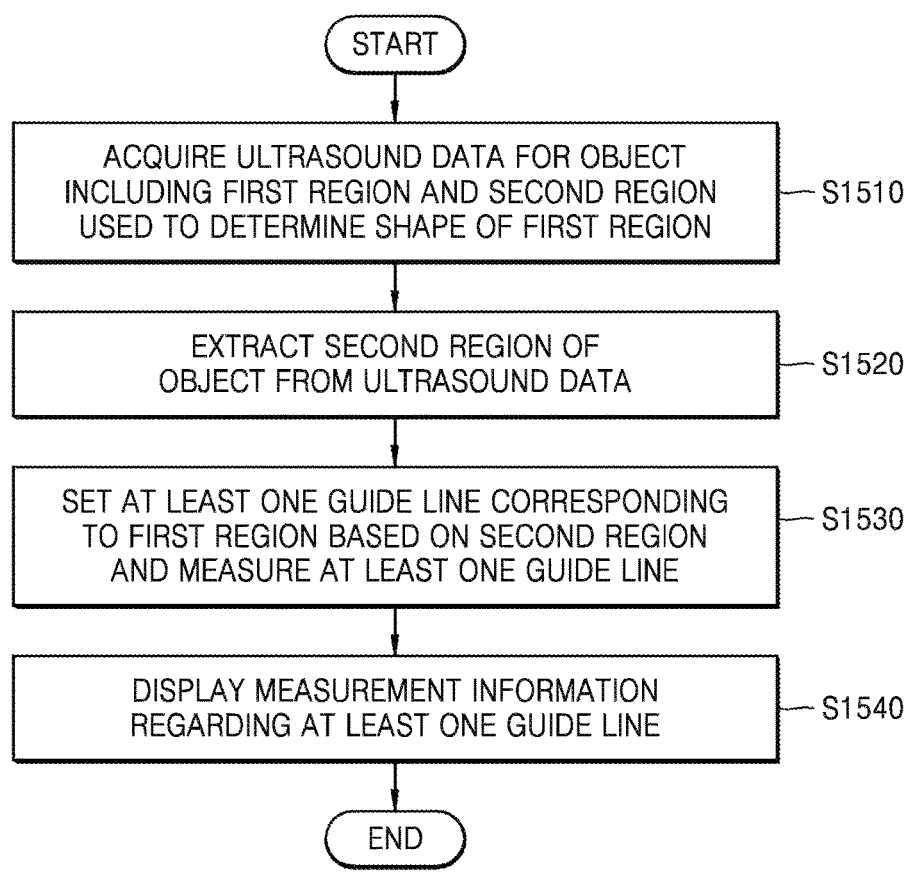
FIGS. 15 and 16 are flowcharts of methods of operating an ultrasound imaging apparatus, according to exemplary embodiments.
Figure 16:
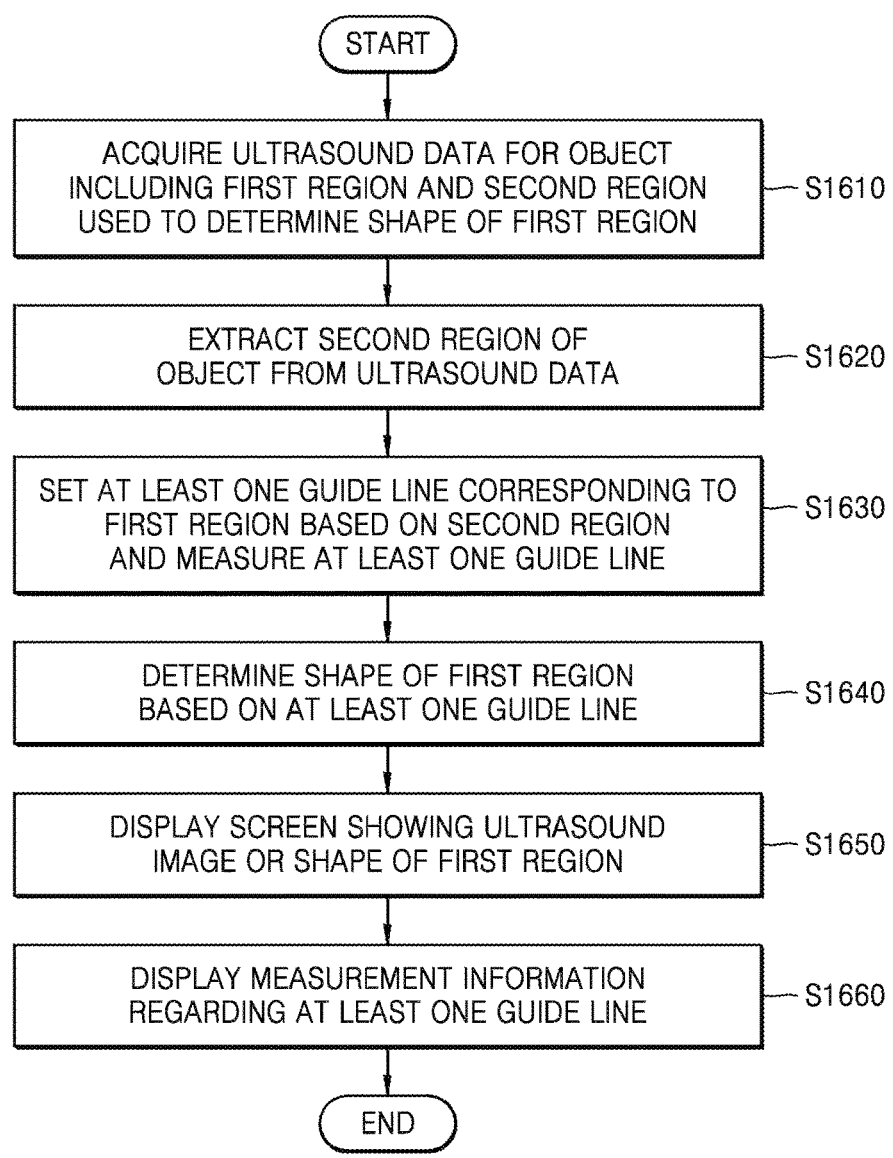

FIGS. 15 and 16 are flowcharts of methods of operating an ultrasound imaging apparatus, according to exemplary embodiments.

Referring to FIG. 15, the ultrasound imaging apparatus acquires ultrasound data for an object including first and second regions (S1510). In this case, the second region is used to determine a shape of the first region. For example, the first and second regions may be a cervix of a pregnant woman and a fetal head region that is near the cervix, respectively. Information about the cervix and the fetal head region is needed to determine a status of the health of the.

The ultrasound imaging apparatus extracts the second region of the object from the ultrasound data (S1520). For example, the ultrasound imaging apparatus may extract a fetal head region located near a cervix from the ultrasound data.

The ultrasound imaging apparatus sets at least one guide line corresponding to the first region based on the extracted second region and controls the at least one guide line to be measured (S1530). For example, the ultrasound imaging apparatus may set at least one of a boundary line of a fetal head region, a boundary line corresponding to a funnel length of a cervix, and a boundary line corresponding to a CL and control the at least one boundary line to be measured.

The ultrasound imaging apparatus displays measurement information regarding the at least one guide line (S1540). For example, the ultrasound imaging apparatus may display information about a funnel length and a CL.

FIG. 16 is a flowchart of a method of operating an ultrasound imaging apparatus, according to another exemplary embodiment. Since operations S1610, S1620, and S1630 shown in FIG. 16 respectively correspond to operations S1510, S1520, and S1530, the same descriptions as already presented with respect to FIG. 15 are omitted.

Referring to FIG. 16, the ultrasound imaging apparatus determines a shape of a first region based on at least one guide line (S1640). The ultrasound imaging apparatus may determine the shape of the first region to be a first shape among a plurality of predesignated shapes by using the at least one guide line. For example, a plurality of predesignated shapes representing a shape of a cervix may be "T", "V", "Y", and "U" types. The ultrasound imaging apparatus may determine the shape of the cervix to be one of the "T", "V", "Y", and "U" types.

The ultrasound imaging apparatus displays a screen showing an ultrasound image obtained from ultrasound data or the shape of the first region (S1650). In detail, the ultrasound imaging apparatus displays a schematic diagram corresponding to the shape of the first region on the screen. Furthermore, the ultrasound imaging apparatus may indicate at least one line corresponding to the at least one guide line on the schematic diagram.

Furthermore, the ultrasound imaging apparatus displays the ultrasound image and a histogram corresponding to at least one position included in the first region. The ultrasound imaging apparatus may indicate the at least one position corresponding to the histogram on the ultrasound image while simultaneously displaying the histogram.

For example, the ultrasound imaging apparatus may display at least one of a schematic diagram corresponding to a shape of a cervix, an icon corresponding thereto, and a histogram corresponding to at least one position included in the cervix.

The ultrasound imaging apparatus displays measurement information regarding the at least one guide line (S1660).

The apparatuses described above may be implemented using hardware components, software components, or a combination thereof. For example, the apparatuses and components illustrated in the exemplary embodiments may be implemented using one or more general-purpose or special-purpose computers, such as a processor, a controller, an arithmetic logic unit (ALU), a digital signal processor, a microcomputer, a field programmable array (FPA), a programmable logic unit (PLU), a microprocessor or any other device capable of responding to and executing instructions in a defined manner.

A processing device may run an operating system (OS) and one or more software applications running on the OS. The processing device also may access, store, manipulate, process, and create data in response to execution of software.

For convenience, although a single processing device may be illustrated for convenience, one of ordinary skill in the art will appreciate that a processing device may include a plurality of processing elements and/or a plurality of types of processing elements. For example, a processing device may include a plurality of processors or a processor and a controller. In addition, the processing device may have different processing configurations such as parallel processors.

Software may include a computer program, a piece of code, an instruction, or one or more combinations thereof and independently or collectively instruct or configure the processing device to operate as desired.

Software and/or data may be embodied permanently or temporarily in any type of machine, component, physical equipment, virtual equipment, computer storage medium or device, or in a transmitted signal wave so as to be interpreted by the processing device or to provide instructions or data to the processing device. The software also may be distributed over network-coupled computer systems so that the software is stored and executed in a distributed fashion. In particular, the software and data may be stored in one or more computer-readable recording media.

The methods according to the exemplary embodiments may be recorded in non-transitory computer-readable media including program instructions to implement various operations embodied by a computer. The media may also include, alone or in combination with the program instructions, data files, data structures, and the like. The program instructions recorded in the media may be designed and configured specially for the exemplary embodiments or be known and available to those skilled in computer software.

Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as ROM, RAM, flash memory, and the like.

Examples of program instructions include both machine code, such as produced by a compiler, and higher level code that may be executed by the computer using an interpreter.

The above-described hardware devices may be configured to act as one or more software modules in order to perform the operations of the above-described embodiments, or vice versa.

While one or more exemplary embodiments have been described with reference to the figures, it will be understood by those of ordinary skill in the art that various modifications and changes in form and details may be made from the above descriptions without departing from the spirit and scope as defined by the following claims. For example, adequate effects may be achieved even if the above techniques are performed in a different order than described above, and/or the aforementioned elements, such as systems, structures, devices, or circuits, are combined or coupled in different forms and modes than as described above or be replaced or supplemented by other components or their equivalents.

Thus, the scope of the present inventive concept is defined not by the detailed description thereof but by the appended claims and their equivalents.

What is claimed is:

1. An ultrasound imaging apparatus comprising:
   a data acquisition unit configured to acquire ultrasound data for an object including a cervix;
   a controller configured to:
     measure at least one guide line corresponding to the cervix based on the acquired ultrasound data, and
     determine a shape of the cervix based on the at least one guide line; and
   a display configured to display measurement information, including information about the shape of the cervix obtained from the at least one guide line.

2. The ultrasound imaging apparatus of claim 1, wherein the data acquisition unit acquires ultrasound data including a fetal head region of the object.

3. The ultrasound imaging apparatus of claim 2, wherein the at least one guide line comprises at least one selected from a boundary line of the fetal head region, a boundary line corresponding to a funnel length of the cervix, and a boundary line corresponding to a cervical length of the cervix, all the boundary lines being indicated on an ultrasound image generated based on the ultrasound data.

4. The ultrasound imaging apparatus of claim 1, wherein the measurement information further comprises at least one selected from a funnel length of the cervix, a cervical length of the cervix, and a histogram corresponding to at least one position included in the cervix.

5. The ultrasound imaging apparatus of claim 3, wherein the controller extracts the fetal head region based on the at least one guide line, extracts a funneling region and the funnel length based on the fetal head region, extracts the cervical length based on at least one of the fetal head region and the funneling region, and determines a shape of the cervix based on at least one of the funnel length and the cervical length.

6. The ultrasound imaging apparatus of claim 1,
   wherein the display displays a screen depicting the determined shape of the cervix.

7. The ultrasound imaging apparatus of claim 1, wherein the display displays an ultrasound image obtained using the ultrasound data.

8. The ultrasound imaging apparatus of claim 7, wherein the display displays a screen in which the at least one guide line is indicated on the ultrasound image.

9. The ultrasound imaging apparatus of claim 8, further comprising a user interface configured to receive an input for editing the at least one guide line indicated on the ultrasound image.

10. The ultrasound imaging apparatus of claim 6, wherein the display displays a schematic diagram corresponding to the determined shape of the cervix on the screen.

11. The ultrasound imaging apparatus of claim 10, wherein the display indicates at least one line corresponding to the at least one guide line on the schematic diagram.

12. The ultrasound imaging apparatus of claim 7, wherein the display displays a histogram corresponding to at least one position included in the cervix and indicates the at least one position on the ultrasound image.

13. The ultrasound imaging apparatus of claim 6, wherein the controller determines the shape of the cervix to be a first shape among a plurality of predesignated shapes by using at least one guide line, and
wherein the display displays a screen showing the shape of the cervix determined to be the first shape.

14. A method of operating an ultrasound imaging apparatus, the method comprising:
acquiring ultrasound data for an object including a cervix;
measuring at least one guide line corresponding to the cervix based on the acquired ultrasound data;
determining a shape of the cervix based on the at least one guide line; and
displaying measurement information, including information about the shape of the cervix, obtained from the at least one guide line.

15. The method of claim 14, further comprising acquiring ultrasound data including a fetal head region of the object.

16. The method of claim 15, wherein the at least one guide line comprises at least one selected from a boundary line of the fetal head region, a boundary line corresponding to a funnel length of the cervix, and a boundary line corresponding to a cervical length of the cervix, all the boundary lines being indicated on an ultrasound image generated based on the ultrasound data.

17. The method of claim 14, wherein the displaying of the measurement information, further comprises displaying at least one selected from a funnel length of the cervix, a cervical length of the cervix, and a histogram corresponding to at least one position included in the cervix.

18. The method of claim 14, further comprising:
displaying a screen depicting the determined shape of the cervix.

19. The method of claim 18, wherein the displaying of the screen depicting the determined shape of the cervix comprises displaying at least one selected from a schematic diagram corresponding to the shape of the cervix, an icon corresponding to the shape of the cervix, and a histogram corresponding to at least one position included in the cervix.

20. The method of claim 19, wherein the displaying of the screen depicting the determined shape of the cervix comprises indicating at least one line corresponding to the at least one guide line on the schematic diagram.

21. The method of claim 18, further comprising:
displaying a histogram corresponding to at least one position included in the cervix; and
indicating the at least one position on an ultrasound image.

22. The method of claim 14, further comprising displaying an ultrasound image obtained using the ultrasound data.

23. The method of claim 22, wherein the displaying of the ultrasound image comprises displaying a screen in which the at least one guide line is indicated on the ultrasound image.

24. The method of claim 23, further comprising receiving an input for editing the at least one guide line indicated on the ultrasound image.

25. A non-transitory computer-readable recording medium having recorded thereon a program for executing a method of operating an ultrasound imaging apparatus, the method comprising:
acquiring ultrasound data for an object including a cervix;
measuring at least one guide line corresponding to the cervix based on the acquired ultrasound data;
determining a shape of the cervix based on the at least one guide line; and
displaying measurement information, including information about the shape of the cervix, obtained from the at least one guide line.

* * * * *